(12) United States Patent
Papp et al.

(10) Patent No.: US 7,754,465 B2
(45) Date of Patent: Jul. 13, 2010

(54) DECONTAMINATION OF BIOLOGICAL AGENTS

(76) Inventors: James A Papp, P.O. Box 882191, Steamboat Springs, CO (US) 80488; Guy Adam Wojtowicz, 2655 Northridge La. North, West Lakeland, MN (US) 55082; Douglas Alan Rice, 980 Deer Meadow Way, Livermore, CO (US) 80536

( * ) Notice: Subject to any disclaimer, the term of this patent is extended or adjusted under 35 U.S.C. 154(b) by 618 days.

(21) Appl. No.: 11/412,243

(22) Filed: Apr. 27, 2006

(65) Prior Publication Data

US 2007/0254048 A1 Nov. 1, 2007

(51) Int. Cl.
*C12N 1/36* (2006.01)
(52) U.S. Cl. .................. 435/245; 424/695; 435/262
(58) Field of Classification Search ................ 424/745; 435/245
See application file for complete search history.

(56) References Cited

U.S. PATENT DOCUMENTS 5,072,004 A * 12/1991 Pettit .......................... 549/267

2005/0013883 A1 * 1/2005 Becker ....................... 424/745

OTHER PUBLICATIONS

Rice, Effective Destruction of *Bacillus atrophaeus* a *Bacillus anthracis* analog using calcium polysulfide, Colorado State, 2006.*
The Columbia Encyclopedia, Sixth Edition, 2001-2005 http://www.bartleby.com/65/li/limesulf.html.*
Janssen,Lincoln Journal Star Newspaper Sunday ed., Lime-sulfur: a fungicide used to control a variety of diseases, Feb. 2002 http://lancaster.unl.edu/hort/Articles/2002/lime-sulfur.shtml.*
MSDS, 1998 Lime sulfur solution.*
Household products databse, 2004.*
www.animalhelp.com/pets/diseasedetail.cfm?disease=20.*
http://web.archive.org.*
http://www.earthtym.net/ref-ringworm.htm.*
U.S. Appl. No. 10/839,869, filed May 2004, Papp, James.*

* cited by examiner

*Primary Examiner*—Jon P Weber
*Assistant Examiner*—Tiffany M Gough
(74) *Attorney, Agent, or Firm*—Crawford Maunu PLLC

(57) ABSTRACT

This invention provides a method for killing biological agents utilizing lime sulfur in liquid or powder form.

7 Claims, No Drawings

DECONTAMINATION OF BIOLOGICAL AGENTS

This method of use invention kills or renders nonviable biological agents, utilizing lime sulfur.

BACKGROUND

Biological Warfare is the use of harmful microorganisms, or the toxins they produce, as weapons against people, animals or crops. A small number of these microorganisms could kill millions of people if effectively distributed. Possible bioterrorist activities include the intentional spreading of dangerous diseases such as anthrax and smallpox. In 2001 authorities found that several offices in the United States and other countries had been mailed envelopes containing traces of anthrax bacteria. Several people died from the disease and the United States Government declared the mailings acts of terrorism.

Our vulnerability as a nation is the result of our size, openness and presence around the world. We have overlapping authority and responsibilities when it comes to terrorism. The office of Homeland Security, F.E.M.A., F.B.I., Centers for Disease Control and Prevention, E.P.A., Military, local police and fire to name a few. Immediate evacuation, containment, and decontamination are the desired first responses to a bio-terrorism threat. Currently, these first responses are not possible because they require special products, special equipment, and special training, none of which is readily available nationwide. Some decontamination agents are as harmful to people and the environment as the agent being eradicated. For example, chlorine dioxide is an effective killer of biological agents. It is also an unstable, extremely explosive, toxic gas.

A major challenge to effective, immediate response to a bio-terrorism is identification of a biological agent. The Encyclopedia of Infectious Diseases reports there have been over 15,000 anthrax hoaxes to postal services. These threats resulted in evacuations and disruption of service until it could be determined that each was a hoax. If a decontaminate, such as chlorine dioxide, is used before the suspected agent is identified, people (including the responders) and the environment would be endangered needlessly. Specialized responders are required to determine if a suspected substance is hazardous. Getting the appropriate personnel to the site takes time—and time is critical when facing the threat of bio-terrorism. Lime sulfur can be used immediately, at the first warning that an unidentified biological agent may be present. If the suspected agent is later determined to be a hoax, no lasting harm has been done by this agricultural product.

SUMMARY OF THE INVENTION

This method of use invention involves using lime sulfur, a recognized fungicide in agriculture, to kill or render non viable biological agents.

BACKGROUND DESCRIPTION OF PRIOR ART

This invention relates to the killing of biological agents using lime sulfur.

Encyclopedia Americana Volume 12 2001 pg. 169-180 acknowledges in an article by Jerry T. Walker of The University of Virginia that fungicides used in agriculture as early as 1800 were sulfur compounds. This article only mentions agriculture.

Random House Unabridged Dictionary Second Addition 1993 says the following "Lime Sulfur Chemical. Mixture of lime and sulfur that is boiled in water, used in powdered form or aqueous solution as an insecticide, a fungicide and sheep dip."

This description of uses mentions agriculture and its use on livestock. The reference to the use of lime sulfur as a sheep dip may or may not be significant. Anthrax in antiquity was called "Wool Sorters Disease". We can find no documentation that the purpose of dipping sheep in lime sulfur was to kill anthrax spores.

United States Patent Pending 10,839,869. This patent application is for the use of lime sulfur to kill mold in homes and buildings. It does not mention the use of lime sulfur to decontaminate biological agents. This patent was filed by myself May 7, 2004. The idea to use lime sulfur as a decontamination product was discussed with Guy Wojtowicz and Douglas Rice in November 2005.

ADVANTAGES OF THIS INVENTION

1. Lime Sulfur is an affordable fungicide that has been thoroughly tested in agriculture. It has a M.D.S.S. and is safe enough to ship through the mail. The safety record of this product is excellent and does not pose a threat to the environment when used properly.

2. A comprehensive decontamination program requires a product that is cost effective, environmentally safe, readily available and requires no special training. Lime Sulfur meets all of these criteria.

3. Lime Sulfur, in a liquid form, could be available in hazardous material containers in Post Offices, Government buildings, schools, airports, embassies or other vulnerable locations. In the case of any suspicious substance it could immediately be placed in the lime sulfur solution rendering it harmless until further testing can be done. Think of these containers as Bioterrorism Fire Extinguishers.

4. Lime Sulfur air filters could capture airborne spores. The present heating, ventilation, air conditioning systems, are moving air and this air can carry spores and contaminate a structure in a relatively short period of time. Special Lime Sulfur filters could be inserted in ventilation systems to trap and kill spores. Portable units with lime sulfur filters could vacuum up suspicious substances as well as the surrounding air.

5. In any potential bioterrorism attack time is critical. It may not be feasible for special response teams to reach remote locations or in the event of simultaneous attacks be at different locations.

6. First responders could implement all of the above prevention procedures. Local fire departments are equipped with self contained breathing equipment. They have been trained in evacuation procedures, equipment shut downs and the handling of toxic substances.

7. These decontamination procedures could be used by the military. The advantage of using lime sulfur is that it does not have to be used in a contained space as chlorine dioxide must. Lime sulfur can be used outside on weapons, equipment, machinery and even soil contamination.

8. Lime Sulfur is a proven fungicide that is safe, cost effective, readily available and requires not special training as a decontamination agent.

CONCLUSION RAMIFICATIONS AND SCOPE OF INVENTION

The anthrax attack against The United States in 2001 showed we were vulnerable to bioterrorism. Lime Sulfur is a safe, cost effective method, that can be implemented immediately to provide a new level of protection against biological agents.

Various example embodiments are directed to approaches as described in connection with the attached appendix, which forms part of this specification and, therefore, part of this patent document. For example, the above-discussed embodiments directed to using lime sulfur in a fire-extinguisher-type liquid form, in a building ventilation system, in a portable vacuum, or with weapons, equipment, machinery and soil contamination may be implemented using such approaches. Such approaches are implemented, for example, in treating pathogens that affect humans (e.g., human pathogens), such as anthrax.

We claim:

1. A system for rendering human pathogens non-viable, the system comprising:
   a lime sulfur composition that renders a human pathogen non-viable; and
   application means including a filter for applying the lime sulfur composition to a human pathogen to render the human pathogen non-viable.

2. The system of claim 1, wherein the application means includes a vacuum.

3. A system for rendering human pathogens non-viable, the system comprising:
   a lime sulfur composition that renders a human pathogen non-viable; and
   application means for applying the lime sulfur composition to a human pathogen to render the human pathogen non-viable, the application means including
   a pressure vessel that holds the lime sulfur composition under pressure and
   an applicator adapted to apply the lime sulfur composition to human pathogens to render the human pathogens non-viable.

4. The system of claim 3, wherein the pressure vessel is adapted to hold a dry lime sulfur composition powder and wherein the applicator is adapted to apply the powder to the human pathogens.

5. The system of claim 3, wherein the pressure vessel is adapted to hold a liquid lime sulfur composition and wherein the applicator is adapted to spray the liquid onto the human pathogens.

6. A system for rendering human pathogens non-viable, the system comprising:
   a lime sulfur composition that renders a human pathogen non-viable; and
   application means for applying the lime sulfur composition to a human pathogen to render the human pathogen non-viable, the application means including a hazardous material container that holds the lime sulfur composition and that accepts items contaminated with a human pathogen for rendering the human pathogen non-viable.

7. The system of claim 1, further comprising an air moving system adapted to move air contaminated with human pathogens to the application means.

\* \* \* \* \*